US008310681B2

(12) United States Patent
Hogan (10) Patent No.: US 8,310,681 B2
(45) Date of Patent: Nov. 13, 2012

(54) ORTHOGONAL REFERENCE ANALYSIS SYSTEM WITH ENHANCED SNR

(75) Inventor: Josh N. Hogan, Los Altos, CA (US)

(73) Assignee: Compact Imaging, Inc.

( * ) Notice: Subject to any disclaimer, the term of this patent is extended or adjusted under 35 U.S.C. 154(b) by 747 days.

(21) Appl. No.: 12/214,600

(22) Filed: Jun. 21, 2008

(65) Prior Publication Data

US 2008/0317201 A1      Dec. 25, 2008

Related U.S. Application Data

(60) Provisional application No. 60/936,782, filed on Jun. 22, 2007, provisional application No. 61/124,169, filed on Apr. 15, 2008.

(51) Int. Cl.
*G01B 11/02* (2006.01)

(52) U.S. Cl. .................................................. 356/497

(58) Field of Classification Search .................. 356/487, 356/497, 479
See application file for complete search history.

(56) References Cited

U.S. PATENT DOCUMENTS

| 2005/0140984 A1* | 6/2005 | Hitzenberger | 356/497 |
| 2006/0028652 A1* | 2/2006 | Chan et al. | 356/497 |

* cited by examiner

*Primary Examiner* — Tarifur Chowdhury
*Assistant Examiner* — Jonathon Cook (57) ABSTRACT

A method, apparatus and system for non-invasive imagining and analysis involves generating probe radiation and reference radiation that have orthogonal polarization characteristics and controlling the polarization characteristics such that substantially all the back scattered probe radiation co-propagates with controlled amounts of components of the reference radiation, thereby improving signal to noise ratios and hence performance of imaging and analysis systems. A preferred embodiment of the invention includes a rotational sensitive mirror that systematically rotates the polarization vector of higher order components of the reference radiation.

16 Claims, 6 Drawing Sheets

ORTHOGONAL REFERENCE ANALYSIS SYSTEM WITH ENHANCED SNR

CROSS REFERENCES TO RELATED APPLICATIONS

This patent application, claims priority from provisional patent application No. 60/936,782 entitled "Orthogonal Reference OCT System" filed on 22 Jun. 2007 and also claims priority from provisional patent application No. 61/124,169 entitled "An Analysis System with Enhanced SNR" filed on 15 Apr. 2008.

FIELD OF THE INVENTION

The invention relates to non-invasive imaging and analysis techniques such as Optical Coherence Tomography (OCT). In particular it relates to optical imaging and analysis of defects or malignant aspects of targets, such as cancer in skin or human tissue; or monitoring for possible malignancies in organs, such as the eye.

This invention also relates to non-invasive analysis of concentrations of specific components or analytes in a target, such as the concentration of glucose in blood, tissue fluids, tissue, or components of an eye or other biological entities. This invention also relates to analysis or monitoring for manufacturing defects in components for improved quality control.

BACKGROUND OF THE INVENTION

Non-invasive analysis of targets is a valuable technique for acquiring information about systems or targets without undesirable side effects, such as damaging the target or system being analyzed. In the case of analyzing living entities, such as human tissue, undesirable side effects of invasive analysis include the risk of infection along with pain and discomfort associated with the invasive process. In the case of quality control, it enables non-destructive imaging and analysis on a routine basis, for example, for quality control purposes.

Optical coherence tomography (OCT), is a technology for non-invasive imaging and analysis. OCT typically uses a broadband optical source, such as a super-luminescent diode (SLD), to probe and analyze or image a target. It does so by applying probe radiation from the optical source to the target and interferometrically combining back scattered probe radiation from the target with reference radiation also derived from the optical source.

The typical OCT optical output beam has a broad bandwidth and short coherence length. The OCT technique involves splitting the output beam into a probe and reference beam, typically by means of a beam splitter, such as a pellicle, a beam splitter cube or a fiber coupler. The probe beam is applied to the system to be analyzed (the target). Light is scattered by the target, some of which is back scattered to form a back scattered probe beam, herein referred to as signal radiation.

The reference beam is typically reflected back to the beam splitter by a mirror. Light scattered back from the target is combined with the reference beam, also referred to as reference radiation, by the beam splitter to form co-propagating reference radiation and signal radiation. Because of the short coherence length only light that is scattered from a depth within the target whose optical path length is substantially equal to the path length to the reference mirror can generate a meaningful interferometric signal.

Thus the interferometric signal provides a measurement of scattering properties at a particular depth within the target. By varying the magnitude of the reference path length (by moving the reference mirror) in a conventional time domain OCT system, a measurement of the scattering values at various depths can be determined and thus the scattering value as a function of depth can be determined, i.e. the target can be scanned.

The reference radiation is typically reflected from a mirror. In addition to generating a useful interferometric signal, the reference radiation also contributes to generating noise in the detector which degrades the signal to noise ratio and hence performance of the system. In order to optimize the signal to noise ratio of typical OCT imaging and analysis systems the magnitude of the reference radiation should be arranged to be compatible with the magnitude of the back scattered optical radiation also referred to herein as the signal radiation.

This is typically achieved in conventional OCT systems by including a fixed attenuation element in the reference beam path. The magnitude of the fixed attenuator is typically selected to maximize signal to noise performance. This involves a compromise between having a low attenuator value to maximize the amplification of the back scattered radiation (by having a high intensity reference level) and having a high attenuator value to minimize the detector noise associated with a high intensity reference level.

The attenuation level is typically selected as a compromise between these two competing considerations. This technique is described in the paper titled "A Simple Intensity Noise Reduction Technique for Optical Low-Coherence Reflectometry" by authors W. V. Sorin and D. M. Baney published in IEEE PHOTONICS TECHNOLOGY LETTERS, Vol. 4, No. 12, Pages 1404-1406, December 1992.

This compromise is further exacerbated in the multiple reference analysis systems and frequency resolved imaging systems described in patent application Ser. No. 11/025,698 filed on 29 Dec. 2004 titled "A Multiple Reference Analysis System" and patent application Ser. No. 11/048,694 filed on 31 Jan. 2005 titled "Frequency Resolved Imaging".

In such systems there is typically a significant portion of the reference radiation that is unwanted or valueless for signal detection and therefore only contributes to generating detector noise and hence degrades the signal to noise ratio, commonly abbreviated as SNR.

Various techniques for minimizing the magnitude of the portion of the reference radiation that is unwanted or valueless for signal detection are described in patent application Ser. No. 11/789,278 filed on 23 Apr. 2007 titled "Optimized Reference Level Generation". These techniques, however, add additional complexity and cost to such systems.

Furthermore, typical OCT systems use a non-polarized beam splitter to generate probe and reference radiation. A disadvantage of this approach is that because the beam splitter is non-polarized typically only fifty percent of the back-scattered probe radiation is directed towards the detector, thus reducing the achievable signal to noise ratio of the analysis system.

Other OCT systems, such as Fourier domain OCT using either a wavelength scanning swept source or a diffraction grating (spectrometer) for wavelength separation, similarly have components of the reference radiation that are not useful for signal detection and therefore only contribute to generating detector noise. In the case of Fourier domain OCT using a diffraction grating, this further exacerbates a problematic "DC component" in the interference signal.

With all of the above approaches, there is a compromise between combining a maximum amount of the scattered probe radiation with an optimum intensity reference radiation so as to optimize signal to noise aspects of the analysis system. These approaches suffer from either additional complexity or introduce problematic noise generating aspects associated with unwanted or valueless co-propagating reference radiation components.

There is therefore an unmet need for a method, apparatus and system for combining a maximum amount of the scattered probe radiation with an optimized amount of reference radiation or reference radiation components while minimizing the problematic noise generating aspects of unwanted or valueless co-propagating reference radiation components at one or more detectors, such a method, apparatus and system providing enhanced signal to noise ratios and thereby improved non-invasive analysis system.

SUMMARY OF THE INVENTION

The invention taught herein meets at least all of the aforementioned unmet needs. The invention provides a method, apparatus and system for non-invasive imagining and analysis wherein generated probe radiation and reference radiation have orthogonal polarization characteristics. In the embodiments taught herein scattered probe radiation forms signal radiation.

Polarization characteristics are controlled such that substantially all the signal radiation co-propagates with controlled or modified amounts of components of the reference radiation, thereby improving signal to noise ratios. Improved signal to noise ratios enhance the imaging and analysis capability of the inventive system.

The preferred embodiment of the invention includes a rotational sensitive mirror that systematically rotates the polarization vector of higher order components of the reference radiation. The inventive method for analyzing a target of interest includes the steps generating probe radiation and reference radiation that have orthogonal polarization characteristics; modifying the polarization characteristics; capturing at least part of the probe radiation scattered from within the target to form signal radiation; combining the signal radiation and at least some of the reference radiation to form co-propagating radiation, wherein said co-propagating radiation is composed of maximized signal radiation and optimized amounts of reference radiation components; detecting at least one interferometric signal generated by at least part of the co-propagating radiation to form an electronic signal; and processing the electronic signal to achieve non-invasive analysis of the target.

In the preferred embodiment of the invention polarization characteristics are modified to maximize signal radiation by rotating the polarization vector of the signal radiation. Polarization characteristics are also modified by rotating at least some of the polarization vectors of components of the reference radiation by means of a rotational sensitive mirror whereby those co-propagating components corresponding to at least some deeper regions of the target have larger magnitudes than co-propagating components corresponding to less deep regions of the target thereby forming optimized amounts of reference radiation components.

The magnitude of the "DC component" of reference radiation co-propagating with the signal radiation and other components of the reference radiation is minimized thereby further optimizing the reference radiation co-propagating with the signal radiation to one or more detectors.

An alternate embodiment of the invention includes a polarized beam splitter with a finite extinction ratio that allows an attenuated portion of the reference radiation to co-propagate with the signal radiation to a detector. In this embodiment the co-propagating radiation that reaches the detector is composed of maximized signal radiation and optimized amounts of reference radiation components or reference radiation components.

The preferred system includes a broadband optical source, such as an SLD which, generates broadband collimated output radiation which is applied to a polarization optic which may be either a half wave plate or a quarter wave plate. The resulting radiation is applied to a first polarized beam-splitter to generate probe radiation and reference radiation that have orthogonal linear polarization. The probe radiation is passed through a quarter wave plate and applied to the target. Backscattered radiation from the target again passes through the quarter wave plate and is applied to the first polarized beam-splitter to form signal radiation directed towards a detection system.

The reference radiation is directed through a partially reflective mirror to a rotational sensitive mirror mounted on a modulating device. Multiple reflections between the partially reflective mirror and the rotational sensitive mirror generate multiple components or orders of reference radiation. The rotational sensitive mirror systematically rotates the plane of polarization with each reflection to generate reference radiation such that larger magnitudes of higher order components pass through the first polarized beam splitter to co-propagate with the signal radiation.

Substantially all of the radiation reflected from the partially reflective mirror back towards the first polarized beam splitter is directed by the first polarized beam splitter away from the detection system. The co-propagating radiation comprised of signal and reference radiation is applied to a second polarized beam splitter, oriented at 45 degrees to generate true and complementary or balanced interference signals in a pair of detectors.

The alternate embodiment of the system is in many respects similar to the preferred system, however the alternate embodiment uses a conventional high reflective mirror in place of the rotational sensitive mirror of the preferred embodiment. Leakage through a polarized beam splitter with a finite extinction ratio enables reference radiation or reference radiation components to co-propagate with the signal radiation and generate an interference signal in a detector.

DETAILED DESCRIPTION OF THE INVENTION

A preferred embodiment of this invention is illustrated in and described with reference to FIG. 1. The preferred embodiment includes a broadband optical source 101, such as an SLD which, generates broadband collimated output radiation 102 which is applied a polarization optic 103. The polarization optic 103 may be either a half wave plate or a quarter wave plate. In the case of a half wave plate, the half wave plate rotates the polarization of the output radiation 102 such that when the output radiation 102 is applied to a polarized beam-splitter 104, the radiation 102 is split into probe radiation 105 and reference radiation 106.

In the case that the polarization optic 103 is a quarter wave plate, the quarter wave plate transforms linearly polarized radiation onto circularly polarized radiation such that when the output radiation 102 is applied to a polarized beam-splitter 104, the radiation 102 is split into probe radiation 105 and reference radiation 106.

The probe radiation 105 and reference radiation 106 have orthogonal polarization characteristics: they are both linearly polarized and are orthogonally linearly polarized with respect to each other. The electric field vector of one is orthogonal to the electric field vector of the other and the magnetic field vector of one is orthogonal to the magnetic field vector of the other thus constituting two orthogonal polarization characteristics. A consequence of being orthogonally linearly polarized is that, if they are combined, for example by a beam-splitter, they may not generate an interference signal. For purposes of this invention "interference signal" and "interferometric signal" are equivalent and interchangeable and can refer to a composite signal which can include multiple interference signals, typically each in a different frequency range.

The probe radiation 105 is passed through a quarter wave plate 107 and applied to the target 108. Back-scattered radiation from the target again passes through the quarter wave plate 107 and is applied to the polarized beam-splitter 104. This back-scattered radiation applied to or "captured" by the beam-splitter 104 is herein referred to as signal radiation.

The double pass of radiation through the quarter waveplate 107 rotates the polarization of this signal radiation by ninety degrees such that it is now directed by the polarized beam-splitter 104 towards a second polarized beam-splitter 109 and a detector 110. The second polarized beam-splitter 109, can also direct the signal radiation towards an optional second detector 111.

The reference radiation 106 is directed to a partial reflective element 112 and a second reflective element 113 mounted on a modulating device 114. The modulating device may be a Piezo device or voice coil that translates the reflective element 113 along the line of propagation of the reference radiation. The reference radiation undergoes multiple reflections between the partial reflective element 112 and the second reflective element 113 to form composite or multiple reference radiation.

Further description of generation of composite or multiple reference radiation can be found in patent applications Ser. No. 11/025,698 filed on 29 Dec. 2004 titled "A Multiple Reference Analysis System" and Ser. No. 11/048,694 filed on 31 Jan. 2005 titled "Frequency Resolved Imaging".

In the preferred embodiment the second reflective element 113 is highly reflective for linear polarization radiation at a first rotational orientation of the mirror about the axis normal to the mirror and its equivalent orientation 180 degrees from the first rotational orientation. The reflectivity of this rotational sensitive mirror decreases as it is rotated about the normal axis, reaching a minimum when it is substantially 90 degrees rotated from the first rotational orientation.

The rotational sensitive mirror 113 is aligned such that it has maximum reflectivity for linear polarized radiation whose polarization vector is orientated at an angle that is rotated 45 degrees from the polarization vector of the linearly polarized incident reference radiation. The direction of the polarization vector of the linearly polarized incident reference radiation is referred to herein as the direction of the original reference radiation polarization.

Figure 2:
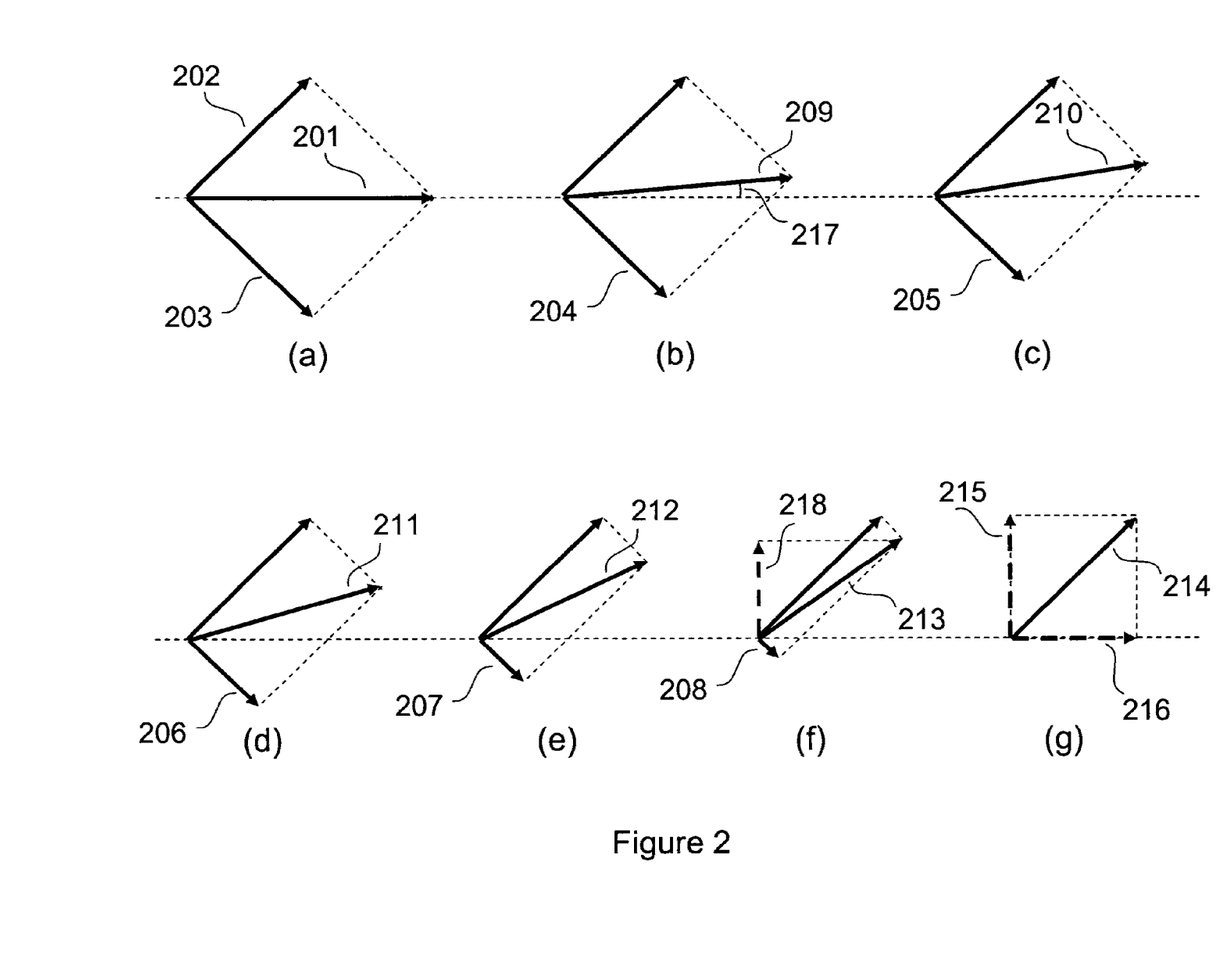
FIG. 2 is an illustration of the sequential systematic rotation of linearly polarized radiation by a rotational sensitive mirror.

The effect of the rotational sensitive mirror 113 on radiation undergoing multiple reflections between reflective elements 112 and 113 is illustrated in FIG. 2. The direction of linear polarization of the reference radiation initially incident on the rotational sensitive mirror 113 is indicated by the vector 201 of FIG. 2(a) (and is referred to as the direction of the original reference radiation polarization).

This vector 201 can be considered as being comprised of the two orthogonal components 202 and 203. In the illustration of FIG. 2 the highly reflective orientation of the rotational sensitive mirror 113 is aligned with the component 202.

With successive reflections between the reflective surfaces 112 and 113 the component 203 that is aligned with the less reflective polarization direction is reduced in magnitude with each reflection. The lower reflectivity causes the reflective magnitude of the 203 component to be systematically reduced, as indicated by diminishing magnitude of components 203, 204, 205, 206, 207 and 208 of FIGS. 2(a), 2(b), 2(c), 2(d), 2(e) and 2(f).

A consequence of the systematic reduction of the 203 component is the systematic rotation of the total or resultant polarization vector as indicated by the rotating vectors 201, 209, 210, 211, 212, 213 and 214 of FIGS. 2(a), 2(b), 2(c), 2(d), 2(e), 2(f) and 2(g). The illustration of vector 214 in FIG. 2(g) indicates a resulting polarization vector aligned with the highly reflective orientation. In the preferred embodiment the polarization direction of further or higher order reflections will remain substantially at this orientation.

The illustration in FIG. 2 shows a polarization rotation of approximately 7.5 degrees per reflection. This is indicated by angle 217 of FIG. 2(b). The systematic rotation results in a total rotation of approximately 45 degrees with six reflections. This magnitude is for illustrative purpose only. The actual magnitude of the rotation depends on the relative reflectivity of the highly reflective and the less reflective properties of the rotational sensitive mirror 113. The relative magnitude of the highly and less reflective property can be selected to achieve a desired rotation per reflection to optimize for specific applications.

The illustration in FIG. 2 also shows the relative magnitude of the components 202, 203 as the 203 component systematically decreases. With each reflection at the partial reflective element 112, the reference radiation reflected back to the second reflective element 113 will be reduced in magnitude because a portion will be transmitted through the partial reflective element 112 to contribute to the reference radiation used in the detection process. In the preferred embodiment the partial reflective element is a partial mirror.

Because of the reduction in magnitude due to transmission through the partial reflective element 112, both components 202 and 203 of FIG. 2(a) and their equivalents in FIG. 2(b), 2(c), 2(d), etc. will be systematically reduced in magnitude with each reflection. The component 214 of FIG. 2(g) would in practice be reduced with respect to component 202 of FIG. 2(a). In FIG. 2, component 214 is shown as being of equal magnitude with component 202 for the illustrative purpose of more clearly depicting the polarization rotation with successive reflections. Furthermore, non-linear (trigonometric) variations in polarization rotation of successive reflections are ignored for illustrative clarity.

The magnitude of the of the reflectivity of the partially reflective element 112 affects the relative magnitude of successive reference radiation reflections. This reflectivity magnitude and the magnitude of rotation per reflection can be selected, to optimize for the relative magnitude of reference radiation components for specific applications.

The component of the reference radiation reflected back towards the polarized beam-splitter 104 by the partially reflective element 112 is still linearly polarized in the direction of the original reference radiation polarization (as it initially emerged from the beam-splitter 104) and is therefore substantially directed away from the second beam-splitter 109 and detector 110. This component of the reference radiation, referred to herein as the DC component, is typically significantly larger than the other components of the reference radiation and typically would generate undesirable noise if directed towards the detector.

Because the DC component is problematic, it is desirable to minimize the amount of the DC component that is directed towards the second beam-splitter 109 and detector 110. Minimizing the amount of the DC component directed towards the second beam-splitter 109 can be achieved by maximizing the extinction ratio of the polarized beam-splitter 104. This approach substantially reduces the amount of the problematic DC component of the reference radiation co-propagating with signal radiation and useful reference radiation towards the detector.

Figure 1:
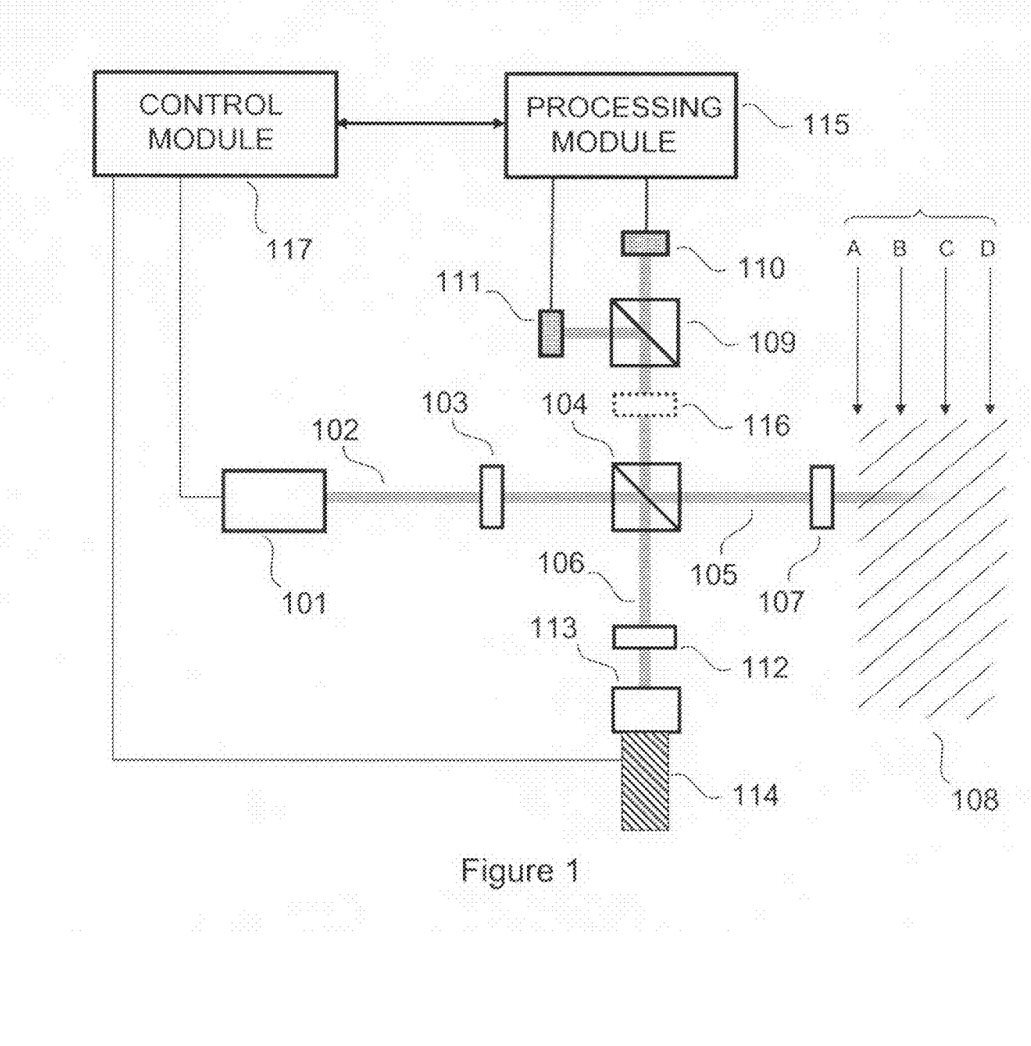
FIG. 1 is an illustration of a preferred embodiment of the analysis system according to the invention.

The useful reference radiation generated by successive reflections between the reflective surfaces 112 and 113 of FIG. 1 contains components that are linearly polarized in the direction orthogonal to the direction of the original reference radiation polarization. These useful reference radiation components substantially pass through the beam-splitter 104 and co-propagate with the signal radiation towards the second beam-splitter 109 and detector 110.

The magnitude of these components that pass through the polarized beam-splitter 104 increases for higher order reflections due to the polarization rotation that occurs with successive reflections. For example, the high order radiation with rotated polarization indicated by vector 214 of FIG. 2(g) can be considered as composed of the two components 215 and 216. The component 216 is polarized along the direction of the original reference radiation.

This component 216 is therefore substantially directed by the beam-splitter 104 away from the second beam-splitter 109 and detector 110. The orthogonal component 215, however, substantially passes through the beam-splitter 104 and co-propagates with the signal radiation towards the second beam-splitter 109 and detector 110.

In the illustrative example of FIG. 2, the magnitude of the useful co-propagating component 215 is 50% of the rotated reference radiation represented by 214. Since there is no further rotation for higher order reflections, such higher order reflections would also have a magnitude of the useful co-propagating component of 50% of their rotated reference radiation. In other words half of the higher order reference radiation will pass through the beam splitter to form useful co-propagating reference radiation. This may also be expressed as 50% of the available photons of the higher order reference radiation will pass through the beam splitter to form useful co-propagating reference radiation.

By comparison with 215 of FIG. 2(g), 218 of FIG. 2(f) is of lower value. This is true because for lower order reflections the magnitude of the useful co-propagating component is less than 50% of the rotated reference as indicated by the magnitude of component 218 of FIG. 2(f) and systematically decreases for lower order reflections. Note, for clarity of depiction, the other lower order components that would co-propagate are not shown. It should also be noted that these are vector quantities are illustrated in FIG. 2.

The relative magnitude of the useful co-propagating components of the rotated reference radiation generated by different order reflections can be optimized for particular applications by (a) selecting the reflectivity of the reflective element 112 and (b) selecting the magnitude of the rotation per reflection which in turn is influenced by the relative reflectivities of orthogonally polarized components.

At this point components of the reference radiation (related to different order multiple reflections) co-propagating with the signal radiation, have a linear polarization orthogonal to the signal radiation and being orthogonal cannot generate an interference signal. The co-propagating reference and signal radiation is applied to the beam-splitter 109 which in the preferred embodiment is orientated substantially at 45 degrees with respect to the direction of polarization of both the co-propagating reference and the signal radiation.

The beam-splitter 109 separates the signal radiation into two orthogonal components, substantially equal in magnitude, one of which is directed at detector 110 and the other directed at detector 111. The beam-splitter 109 also separates the co-propagating reference radiation into two orthogonal components, substantially equal in magnitude, one of which is directed at detector 110 and the other directed at detector 111.

Resulting co-propagating components of the reference and signal radiation generate one interference signal that is detected by detector 110 and an inverted interference signal that is detected by detector 111. The two detected interference signals, also referred to as true and complementary signals can undergo conventional processing in an electronic processing module 115 to achieve balanced or differential detection which can reduce or substantially eliminate common mode noise, such as relative intensity noise of the optical source 101.

This is typically performed in the processing module by summing the signals in an operational amplifier prior to digitizing the resultant signal. This summing may be done prior to or within a typical pre-amplification stage but could also be performed after the detected electronic signals have been digitized. The detected electronic signals are digitized and further processed in the electronic processing module 115 to achieve non-invasive analysis of the target.

A control module 117 coordinates modulating the reflective element 113 and other aspects of the imaging and analysis system with processing the interference signals. In a variation of the preferred embodiment, an additional optic element 116, such as a half-wave plate, is used to rotate the polarization orientation of both the co-propagating reference and the signal radiation by 45 degrees. This eliminates the requirement to have the beam-splitter 109 orientated at 45 degrees.

In the preferred embodiment the quarter-wave plate 107 controls the linear polarization of the probe radiation by circularizing the probe radiation and by re-linearizing the backscattered probe signal on its return pass through the quarter-wave plate 107. The quarter-wave plate 107 thereby controls orthogonal polarization characteristics to form linearly polarized signal radiation whose polarization vectors are rotated by ninety degrees with respect to the original linearly polarized probe radiation. The beam-splitter 104 directs substantially all of the signal radiation towards the detection system.

The beam-splitter 104 and reflective element 113 control components of the reference radiation such that the problematic DC component reflected by the reflective element 112 towards the beam-splitter 104 is substantially all directed away from the detection system by the beam-splitter 104. The beam-splitter 104 combines some components of the reference radiation with the signal radiation such that the components of the reference radiation and the signal radiation co-propagate towards the detection system.

The relative magnitude of the polarization components of higher order components (or multiple reflection orders) of the reference radiation that co-propagate with the signal radiation is determined by the reflective elements 112 and 113. Thus in the preferred embodiment the combination of the quarter-wave plate 107, the beam-splitter 104 and reflective elements 112 and 113 control or modify the relative properties of the orthogonal characteristic of the signal and reference radiation.

Thus the radiation co-propagating to the detection system is composed of maximized signal radiation and optimized amounts of reference radiation components. The signal radiation is maximized by rotating the polarization vector of the signal radiation. The reference radiation is optimized by rotating at least some of the polarization vectors of components of the reference radiation. If all of the multiple reference components, with the exception of the DC component that is reflected from the reflective element 112 back towards the beam-splitter 104, are rotated by 45 degrees then the amount of DC component of reference radiation that co-propagates with the signal radiation to the detection system is minimized. This enables the reflective element 112 to have a very high reflectivity, for example greater than 90% or preferably greater than 95%, while still having little of this DC component reaching the detection system. The high reflectivity of reflective element 112 also causes the magnitude of the components of the multiple radiation reflecting between the reflective elements 112 and 113 to fall of in intensity at a lower rate. Thus if all of these multiple reference components are rotated by 45 degrees then substantially 50% of these components will be directed towards the detection system and they will have substantially the same or only a slightly declining magnitude. This combination of minimizing the un-useful DC component reaching the detection system and having substantially similar magnitudes of the other useful components of the multiple reference radiation optimizes the amounts of reference radiation components to some extent. In the preferred embodiment the relative amounts of reference radiation components are further optimized by a rotational sensitive mirror that rotates the useful multiple reference components such that components corresponding to at least some deeper regions of the target have larger magnitudes co-propagating with the signal radiation to the detection system than copropagating components corresponding to less deep regions of the target and by minimizing the amount of DC component of reference radiation that co-propagates with the signal radiation to the detection system.

The co-propagating signal radiation and controlled or modified magnitudes of components of reference radiation are thus substantially un-accompanied by problematic DC component of the reference radiation. The co-propagating signal and reference radiation is separated by the polarized beam-splitter 109 into two beams of co-propagating radiation of substantially equal magnitude which generate two substantially complementary interferometric signals that are detected by the opto-electronic detectors 110 and 111.

The detected interferometric signals form electronic signals that are processed by conventional electronic processing techniques to achieve non-invasive analysis of the target 108. The preferred embodiment of the invention described above enables maximizing the signal to noise performance of the non-invasive analysis system by controlling or modifying the relative magnitude and direction of polarization of the signal radiation and various components of the reference radiation, or in general, the properties of the orthogonal polarization characteristics of the radiation and the properties of at least some components of the same polarization.

For example, for imaging applications, a small rotation angle 217 of FIG. 2(b) can be selected to minimize the magnitude of co-propagating radiation to detectors of lower order reflections and only achieve the maximum magnitude of co-propagating radiation to detectors for sufficiently high order reflections such that adjacent scans overlap and can therefore yield a continuous composite scan suitable for generating an image of the target. The non-overlapping interference signals related to the weaker lower order components of the reference radiation can be used for other purposes such as front surface location or alignment.

In applications including the non-invasive glucose monitoring, an advantage of minimizing the magnitude of co-propagating radiation of lower order reflections is that it minimizes the interference signal from the skin surface and thus minimizes the digitizing noise of interference signals associated with deeper regions of tissue. It also minimizes or eliminates the requirement for logarithmic amplification.

In another example, the rotation angle 217 of FIG. 2(b) can be selected to achieve maximum magnitude of co-propagating radiation to detectors at a very high order reflection in order to exploit the extended (or amplified) scan capability, without overlapping scans. In this example the separation between the reflective elements 112 and 113 can be large. In such cases the rotational sensitive mirror could be replaced by a wave plate and a conventional highly reflective mirror.

Many variations of the system described in the preferred embodiment are possible. For example, a simpler single ended (as opposed to a balanced) detection system can be configured by replacing the half-wave plate 116 and beam-splitter 109 of FIG. 2 with a linear polarizer orientated at 45 degrees with respect to the direction of polarization of both the co-propagating signal and reference radiation (which are orthogonal or at ninety degrees with respect to each other).

The resulting signal and reference radiation have aligned directions of polarization and can generate an interferometric signal that can be detected by the detector 109 to form (or output) and electronic interferometric signal also referred to as an electronic signal or composite electronic signal.

An alternative embodiment is illustrated in and described with reference to FIG. 3. In this embodiment a broadband optical source 301, such as an SLD which, again generates broadband collimated output radiation 302 which is applied a polarization optic 303 (such as a half wave plate) that rotates the polarization of the output radiation 302 such that when it is applied to a polarized beam-splitter 304 it splits the radiation 302 into probe radiation 305 and reference radiation 306. The probe radiation 305 and reference radiation 306 are linearly polarized and are orthogonally polarized (each with respect to the other).

As in the preferred embodiment, the probe radiation 305 is passed through a polarization optic 307 and applied to the target 308. Back-scattered radiation from the target passes through the polarization optic 307 and is applied to the polarized beam-splitter 304. In this embodiment the polarization optic 307 is a quarter wave-plate. The double pass of the radiation through the quarter wave-plate 307 rotates the polarization of this radiation such that it is now directed by the polarized beam-splitter 304 towards the detector 309.

The captured back-scattered probe radiation referred to as signal radiation 305 also now has the same polarization as the reference radiation 306. The reference radiation is applied to the partial reflective element 309 and a conventional highly reflective or full mirror 310 mounted on the Piezo device 311. The combination of the partial reflective element 309 and the full mirror 310 mounted on the Piezo device 311 generates composite reference radiation as described in patent application Ser. Nos. 11/025,698 and 11/048,694.

As in the preferred embodiment, the reference radiation that does generate useful interference signals, corresponding to the locations such as those indicated be the arrows 313 label "A, B, C and D", does not need to be attenuated but can be the highest intensity compatible with the reflectivity of the partial reflective element 309. The magnitude of this useful reference radiation can be determined by the extinction ratio (or leakage) of the beam-splitter 304.

The composite radiation that is reflected back to the polarized beam-splitter 304 also includes a large portion of radiation reflected by the partial reflective surface 309. This portion of the radiation typically has relatively high intensity and typically does not generate a useful interference signal (unless the optical system is moving with respect to the target).

A substantial portion of this high intensity, but typically unused, portion of the reference radiation is directed by the polarized beam-splitter 304 away from the detector 312 (towards the optical source 301 and therefore does not generate noise in the detector. However a portion of what has been referred to herein as the DC component of the reference radiation is directed towards the detector 312. The magnitude of this portion is determined by the extinction ratio of the beam-splitter 304.

Figure 3:
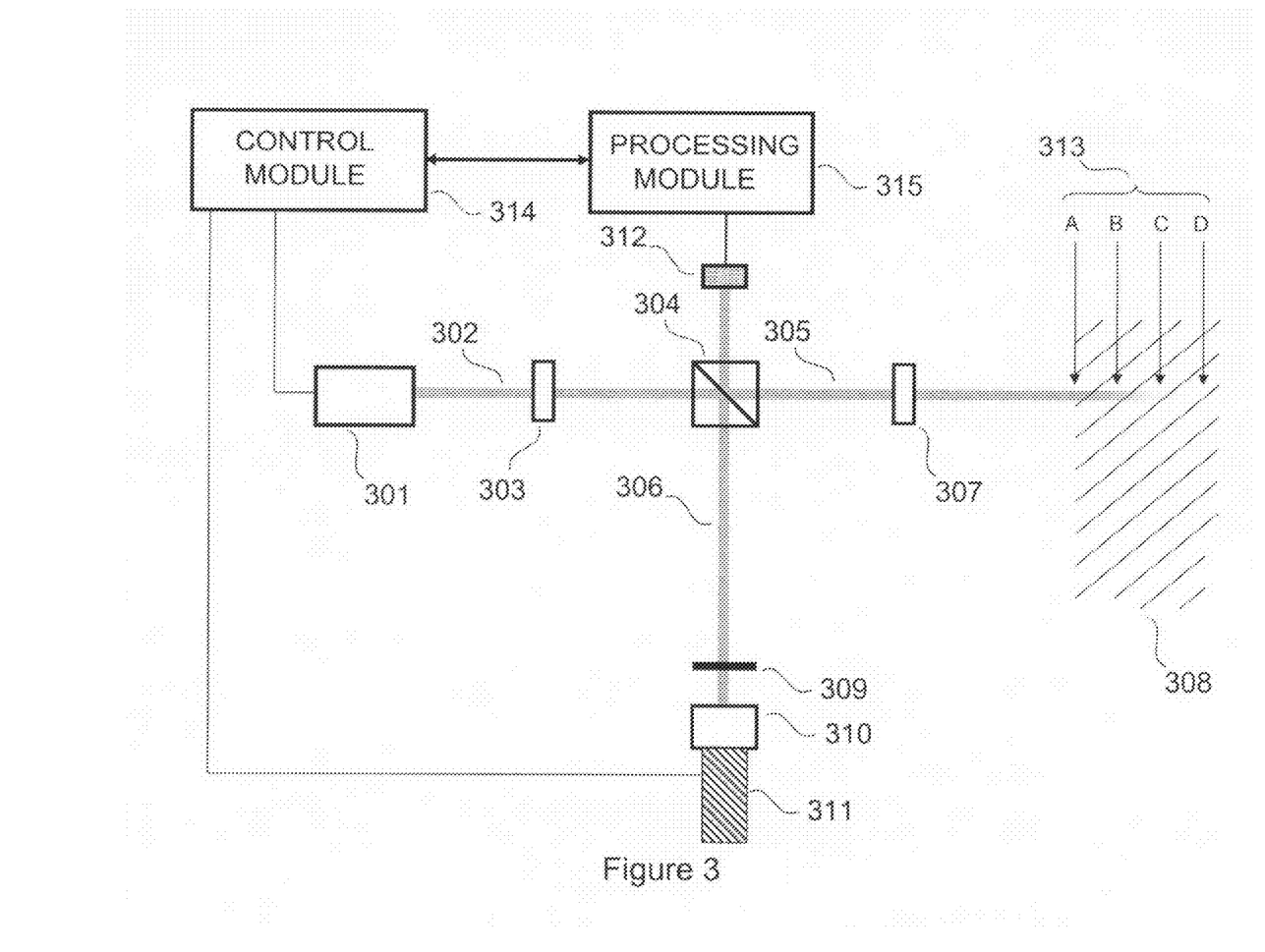
FIG. 3 is an illustration of an alternative embodiment of the analysis system according to the invention.

The embodiment depicted in FIG. 3 has reduced signal to noise performance, as the DC component is applied to the detector and the higher order reference radiation components systematically decrease in magnitude. However, this embodiment does maximize the magnitude of the signal radiation detected and can use a conventional mirror 310. This embodiment also includes control and processing modules 314 and 315 similar to the preferred embodiment (but without the double balanced processing aspect).

Figure 4:
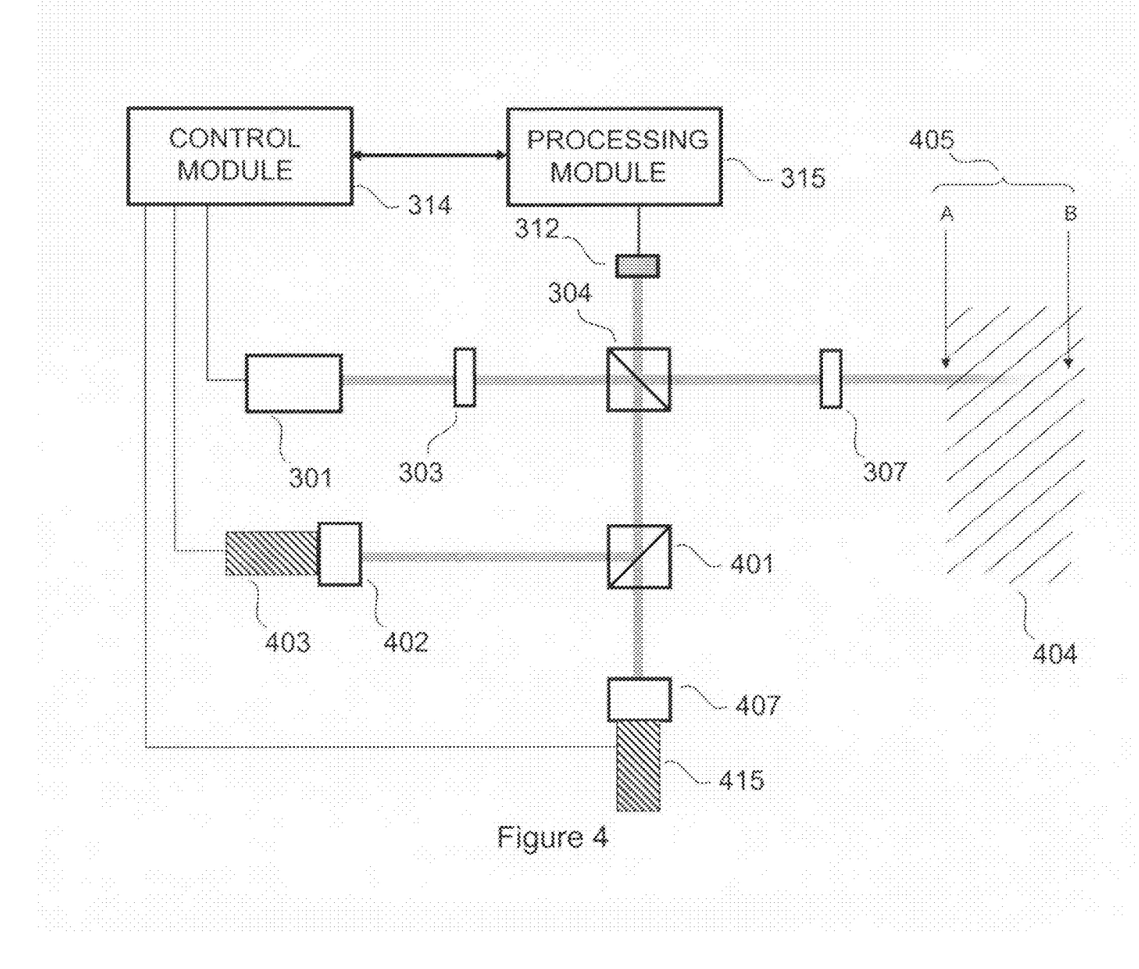
FIG. 4 is an illustration of yet another embodiment of the inventive system.

Another multiple reference embodiment is illustrated in and described with respect to FIG. 4. This is similar in many respects to that illustrated in FIG. 3, with similar elements 301, 303, 304, 307, 312, 314 and 315. However, the partial reflective surface 309 of FIG. 3 is replaced by an additional beam splitter 401 and an additional mirror 402 mounted on an additional Piezo device 403 which generate interference signals related to regions in the target 404 indicated by the arrows 405 labeled "A" and "B".

Variations of these multiple reference arrangements are described in patent application Ser. Nos. 11/025,698 and 11/048,694. The present invention is applicable to these and other variations.

Figure 5:
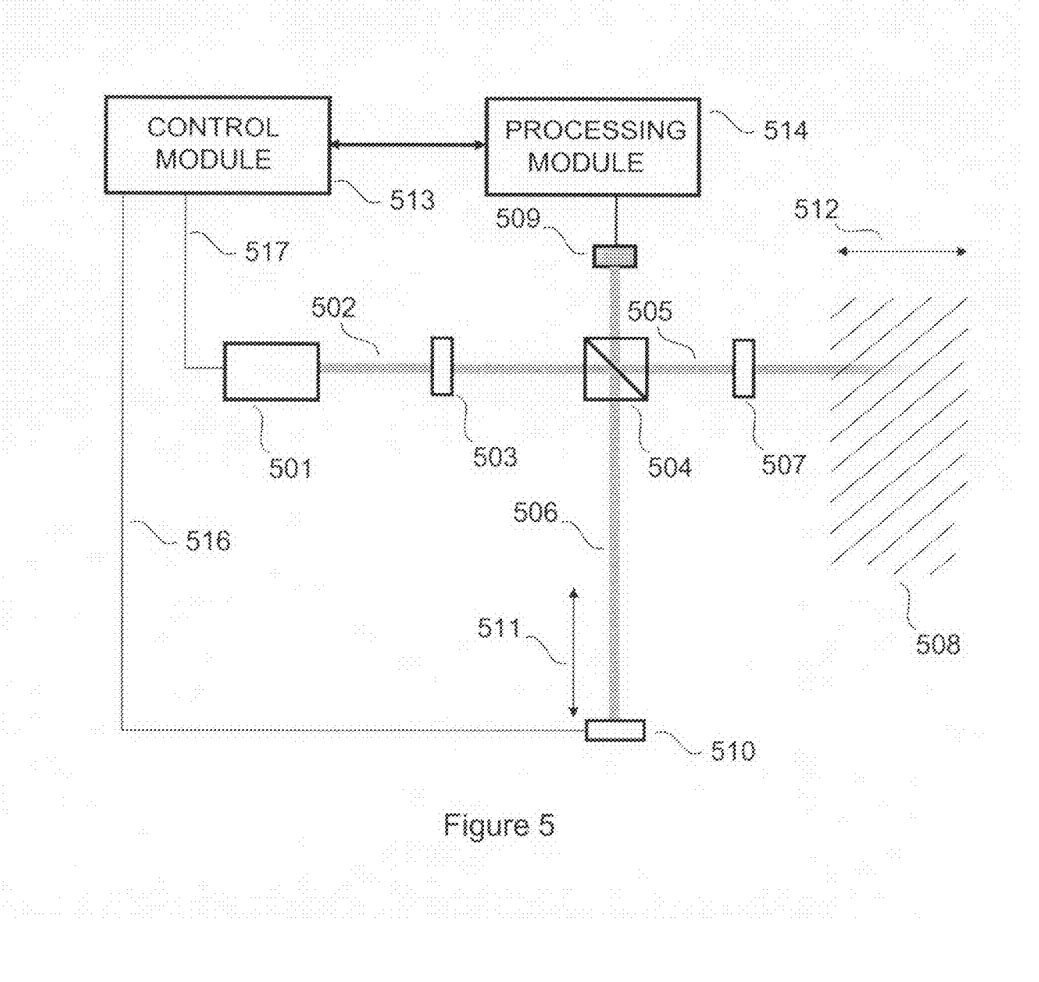
FIG. 5 is an illustration of the inventive system in a conventional time domain OCT application.

An embodiment using a conventional time domain scanning reference mirror is illustrated in and described with respect to FIG. 5. As in the preferred embodiment a broadband source 501 generates radiation 502 which passes through a polarization wave-plate 503 and is applied to a polarized beam-splitter 504 to generate probe radiation 505 and reference radiation 506. The probe radiation 505 is passed through a polarization optic 507 and applied to the target 508.

Back-scattered radiation from the target again passes through the polarization optic 507 and is applied to the polarized beam-splitter 504. This polarization optic 507 controls the orthogonal polarization characteristic of the probe radiation such that the back-scattered probe radiation can generate an interference signal if re-combined with the reference radiation. In this embodiment the polarization optic 507 is a quarter wave-plate. The double pass of radiation through the quarter wave-plate 507 rotates the polarization of this radiation by ninety degrees such that it is now substantially all directed by the polarized beam-splitter 504 towards the detector 509.

The back-scattered probe radiation 505 also now has the same linear polarization as the reference radiation 506 that is reflected back to the polarized beam-splitter 504 by the reference mirror 510. Since the back-scattered probe radiation 505 and the reflected reference radiation 506 have the same polarization they can generate an interference signal.

As the reference mirror 510 is translated through the scanning range 511 the generated interference signal relates to locations within the target spanning a corresponding region of the target indicated by arrow 512. The magnitude of the reference radiation co-propagating with the signal (or back-scattered probe) radiation is determined by the extinction ratio (or leakage) of the polarized beam-splitter 504.

In this embodiment signal to noise performance is optimized by using substantially all of the signal (or back-scattered probe) radiation and an optimal amount of the reference radiation by designing an appropriate extinction ratio of the polarized beam-splitter 504 or by a combination of the extinction ratio and a conventional attenuation element.

As in conventional time domain OCT systems, the reference mirror can be translated by conventional electromechanical or fiber stretcher means, typically controlled by an electronic control module 513. While the reference mirror is translated, the detected interferometric signal is typically acquired and processed by an electronic processing module 514. The processed signal is typically made available for display, further processing or storage.

Another embodiment, similar in many respects to that illustrated in FIG. 5, where the optical source or radiation source 501 is a swept source which emits radiation that changes wavelength (or sweeps through a wavelength change). This is a Fourier domain OCT system in which depth scanning is effectively achieved by wavelength scanning and processing the resulting interference signal. In this embodiment the reference mirror can be stationary.

Figure 6:
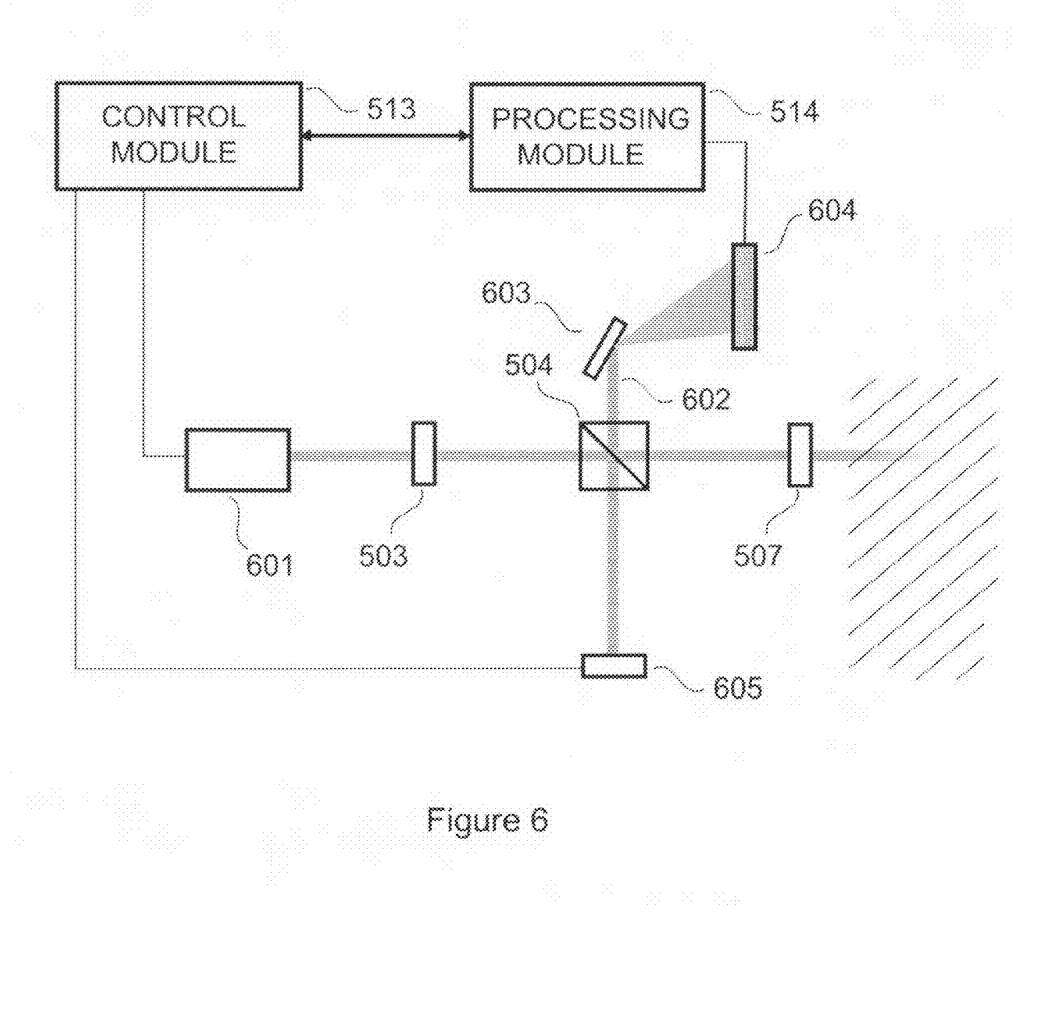
FIG. 6 is an illustration of the inventive system in a Fourier domain OCT system.

Yet another embodiment is illustrated in and described with respect to FIG. 6. This is also similar in many respects to that illustrated in FIG. 5 with similar elements 503, 504, 507, 513 and 514. In this embodiment the optical source (or radiation source) 601 is a broadband source, such as an SLD. However, the interferometric signal 602 is applied to a diffraction grating (or spectrometer) 603 to separate the signal into different wavelength components.

The different wavelength components are detected by a detector array 604, for example a CCD (Charged Coupled Device) array. This is a Fourier domain OCT system in which depth scanning is effectively achieved by detecting the interferometric signal associated with the individual wavelength components and processing the results. In this embodiment the reference mirror 605 can be stationary or optionally translated by a Piezo device for Fourier domain OCT variations, such as sinusoidal phase-modulating interferometry (as depicted in FIG. 6).

It is understood that the above description is intended to be illustrative and not restrictive. Many variations and combinations of the above embodiments are possible. Many of the features have functional equivalents that are intended to be included in the invention as being taught and many other variations and combinations of the above embodiments are possible, for example, various combinations of modulators can be used, including but not limited to: phase modulators: Piezo-electric modulators: mechanically amplified Piezo-electric actuators (to increase length changes). In some embodiments the relative optical path lengths of reference beams could be systematically varied to vary the relative locations from which information is obtained.

The preferred embodiments illustrated are free space configurations. Equivalent configurations could be implemented in optical fiber or in combinations of free space and optical fiber. In such designs or configurations beam-splitters could be replaced by fiber couplers. Mirrors could be replaced by fiber reflective elements, such as fiber loops or Bragg gratings. The preferred embodiments describe back-scattered radiation, however, systems involving transmissive scattered radiation could also be configured.

Embodiments, involving re-arrangements of the preferred embodiment design are included. For example, a quarter wave plate could be inserted in the reference path, rather than the probe (or signal) path. In this case, the DC component of the reference radiation would pass straight through the beam-splitter 104 of FIG. 1 and the useful components of the reference radiation would co-propagate along with substantially all the backscattered probe or signal radiation towards optic 103 (a half-wave plate) of FIG. 1.

In this embodiment, the co-propagating useful components of the reference radiation and the backscattered probe or signal radiation could be separated out by polarization optics. In another embodiment, the radiation passing through the first beam splitter 104 could form the reference radiation and the radiation directed at 90 degrees could form the probe radiation.

Embodiments, both time domain and Fourier domain, that do not include a rotational sensitive element, could also have a quarter wave plate and attenuator between the first beam splitter and a reference element, i.e. between 504 and 510 of FIG. 5; and 504 and 605 of FIG. 6 or between elements 304 and 309 of FIG. 3; and between elements 304 and 401 of FIG. 4. This arrangement would have maximized signal radiation co-propagating with orthogonally polarized reference radiation and would thereby enable balanced detection with an arrangement similar to that of elements 109, 110, 111 and optionally 116 of FIG. 1.

The preferred embodiments are described and illustrated in terms of an optical processing system generating optical probe and reference beams (or radiation), however the invention is not limited to optical radiation. The invention applies to all regions of the electro-magnetic spectrum, including but not limited to, micro-wave or X-ray, and is not restricted to the region conventionally referred to as optical and can include other forms of radiation.

Optical sources, include but are not limited to, light emitting diodes (LED); superluminescent diodes (SLD); laser sources; laser diodes; fiber lasers; wavelength tunable laser diodes; swept source lasers; mode-locked lasers; and continuum generating sources.

Many of the features have functional equivalents that are intended to be included in the invention as taught. For example, the optical source could include multiple SLDs with either over-lapping or non-overlapping wavelength ranges, or, in the case of a mode-locked laser source could be an optically pumped mode-locked laser, it could be a solid state laser, such as a Cr:LiSAF laser optically pumped by a diode laser.

The element rotating the polarization vectors of components of the reference radiation could be a rotational sensitive mirror based on technologies that include but are not limited to: anisotropic thin film; bi-axial materials; multi-layer dielectric stacks; obliquely deposited thin; photonic crystal structures; a reflective element with aligned magnetic properties.

The element rotating the polarization vectors of components of the reference radiation could be a reflective element combined with a magnetic field, such as a Faraday mirror or it could be a reflective element combined with wave plate or optical retarder. Such combinations are herein referred to as a rotational sensitive reflective unit.

The quarter wave plate through which probe radiation passes to the target could be replaced by a Faraday rotator or equivalent to apply linear polarized radiation to the target and yet still have the back scattered radiation rotated by 90 degrees so that substantially all the signal radiation is still directed towards the detection system.

The optical source could be an actively mode-locked laser diode or a passively mode locked by a Kerr lens or a semiconductor saturable absorber mirror. Gain switched optical sources, with optical feedback to lock modes may also be used. For purposes of this invention, mode-locked lasers will include gain switched optical sources. The optical source could be a VCSEL (vertical cavity surface emitting laser), or an LED (light emitting diode) or an incandescent or fluorescent light source or could be arrays of the above sources.

The preferred embodiments include collimated optical sources, however, they could also various combinations of lenses or lens arrays could be employed to collimate the source radiation or to focus the probe radiation into the target or to have converging or diverging beams at the beam splitter. Other examples will be apparent to persons skilled in the art. The scope of this invention should be determined with reference to the specification, the drawings, the appended claims, along with the full scope of equivalents as applied thereto.

What is claimed is:

1. A method of non-invasive analysis of a target, said method comprising:

generating probe radiation and multiple reference radiation that have orthogonal polarization characteristics;

modifying at least some of said polarization characteristics, wherein the step of modifying polarization characteristics further includes the step of rotating components of the multiple reference radiation, with the exception of the DC component, such that the co-propagating radiation contains a minimized amount of DC component of reference radiation, said DC component of reference radiation thereby forming an optimized amount of a reference radiation component;

capturing at least part of said probe radiation scattered from within said target to form signal radiation;

combining said signal radiation and at least some of said reference radiation to form co-propagating radiation, wherein said co-propagating radiation is composed of maximized signal radiation and optimized amounts of at least one component of the multiple reference radiation components;

detecting at least one interferometric signal generated by at least part of said copropagating radiation to form an electronic signal; and processing said electronic signal to achieve non-invasive analysis of said target.

2. The method of claim 1, wherein the step of modifying said polarization characteristics further includes modifying said polarization characteristics to maximize signal radiation by rotating the polarization vector of the signal radiation.

3. The method of claim 1, wherein the step of modifying said polarization characteristics includes rotating at least some of the polarization vectors of components of the reference radiation.

4. The method of claim 3, where the step of modifying polarization characteristics further includes the step of modifying the magnitude of at least some of the components of the reference radiation that are co-propagating with the signal radiation to a detector, such that components of the reference radiation corresponding to at least some deeper regions of the target have larger magnitudes than components of the reference radiation corresponding to less deep regions of the target thereby forming optimized amounts of reference radiation components.

5. The method of claim 3, wherein the step of modifying at least some of said polarization characteristics further includes rotating at least some of the polarization vectors of components of the reference radiation.

6. The method of claim 1, wherein the step of modifying polarization characteristics further includes the step of rotating components of the multiple reference radiation, with the exception of the DC component, such that co-propagating radiation contains a minimized amount of DC component of reference radiation, said DC component of reference radiation thereby forming an optimized amount of a reference radiation component.

7. The method of claim 1, wherein the step of analyzing further includes the step of generating an image of at least some aspects of the target.

8. The method of claim 1, wherein the step of analyzing further includes the step of determining the concentration of a metabolite.

9. The method of claim 8, wherein the step of analyzing further includes the substep of determining glucose concentration.

10. An apparatus for non-invasive analysis of a target, said apparatus comprising:
- a broad band optical source and a polarized beamsplitter for generating probe radiation and multiple reference radiation that have orthogonal polarization characteristics;
- a quarterwave plate for modifying polarization characteristics of signal radiation;
- a partial mirror that leaves the polarization characteristics of the DC components substantially unchanged thereby minimizing the magnitude of the DC component of the reference radiation that co-propagates with the signal radiation; and
- a rotational sensitive mirror for modifying polarization characteristics at least some of components of multiple reference radiation;
- means for capturing at least part of said probe radiation scattered from within said target to form signal radiation;
- means for combining said signal radiation and at least some of said reference radiation to form co-propagating radiation, wherein said co-propagating radiation is composed of maximized signal radiation and optimized amounts of at least one component of the multiple reference radiation components;
- detector for detecting at least one interferometric signal generated by at least part of said co-propagating radiation to form an electronic signal;
- and processing module for processing said electronic signal to achieve non-invasive analysis of said target.

11. The apparatus of claim 10, wherein said quarterwave plate rotates the polarization vector of the signal radiation so as to maximize the magnitude of the signal radiation co-propagating with the reference radiation.

12. The apparatus of claim 10, wherein said rotational sensitive mirror rotates the polarization vectors of at least some components of the reference radiation, thereby modifying the magnitude of co-propagating components of said reference radiation.

13. The apparatus of claim 12, where said rotational sensitive mirror rotates the polarization vectors of components of the reference radiation such that components of the reference radiation corresponding to at least some deeper regions of the target have larger magnitudes than components of the reference radiation corresponding to less deep regions of the target thereby forming optimized amounts of co-propagating reference radiation components.

14. The apparatus of claim 10, wherein the partial mirror/reflective element leaves the polarization characteristics of the DC components substantially unchanged thereby minimizing the magnitude of the DC component of the reference radiation that co-propagates with the signal radiation.

15. The apparatus of claim 10, wherein said optical source is selected from the following: a light emitting diode (LED), a superluminescent diode (SLD), a solid state laser, a laser diode, a fiber laser, a tunable laser diode, a swept source laser, a mode-locked laser, a continuum generating source.

16. The apparatus of claim 10, further comprising a second polarized beam splitter for splitting an interference signal into true and complementary signals for balanced detection.

* * * * *